United States Patent [19]

Blandamura

[11] Patent Number: 4,639,440

[45] Date of Patent: Jan. 27, 1987

[54] THERAPEUTIC USE OF CYPROTERONE ACETATE

[75] Inventor: Manlio Blandamura, Rome, Italy

[73] Assignee: Finchimica S.R.L., Milan, Italy

[21] Appl. No.: 779,421

[22] Filed: Sep. 24, 1985

[30] Foreign Application Priority Data

Jan. 8, 1985 [IT] Italy ................................ 19041 A/85

[51] Int. Cl.⁴ ............................................. A61K 31/56
[52] U.S. Cl. ..................................................... 514/178
[58] Field of Search ........................................ 514/178

[56] References Cited

U.S. PATENT DOCUMENTS 4,367,227  1/1983  Bingham ............................. 514/178

*Primary Examiner*—Elbert L. Roberts
*Attorney, Agent, or Firm*—Oblon, Fisher, Spivak, McClelland, & Maier

[57] ABSTRACT

There is disclosed a new therapeutic use of cyproterone acetate, to block the estrogen signal in the treatment of functional and tumoral estrogen-dependant pathology, in women, caused by intrafollicular iperestrogenism in a pharmaceutically-acceptable dosage.

4 Claims, No Drawings

THERAPEUTIC USE OF CYPROTERONE ACETATE

The present invention refers to a new therapeutic use of 6-chloro-1α,2α-methylene-17α-hydroxy-4,6-pregnadiene-3,20-dione acetate, well known in the literature as cyroterone acetate, having the following structural formula:

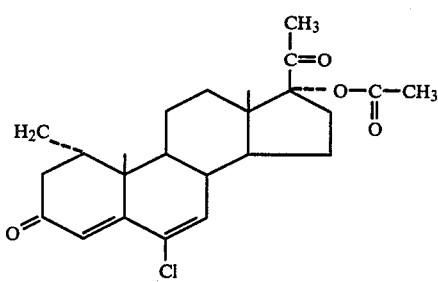

It has been described in the literature the anti-androgen activity of cyproterone acetate, for instance by Iunkmann K. et. al., Acta endocrinol, suppl. 90, 139–54, 1964; Neumann F. et al, Endocrinology 75, 428–33, 1964; Neumann F. et al. Acta Endocrynol. 53, 382–90, 1966; Kramer M. et al., Naunyn-Schimiedelsbergs Arch. Exp. Path. Pham. 251-124-5, 1965; Neumann F., Medizinische Klinik Wachenscr. fuer klinik und Praxis 68 Jahrgang, Heft 11, 329–333, 1973.

Cyproterone acetate as anti-androgen is used in the woman only for the virilization syndromes, such as acne, hirsutism, hypertrichosis.

For the first time, the use of cyproterone acetate as anti-estrogen has been disclosed by the Applicants in the Italian patent application 23191 A/80 (U.S. Pat. No. 4,344,942) for the treatment of cystic glandular hyperplasia of the endometrium and, in general of the pathology supported by extrafollicular (extraovaric) hyperestrogenism being characteristic of menopause and premenopause women.

According to the present invnetion, it has been surprisingly found that the use of cyproterone acetate may be enlarged, with unexpected results, to other gynecologic pathologies not unanimously caused by hyperestrogenism, as the above cystic glandular hyperplasia of the endometrium.

The surprising action of cyproterone acetate consists in inhibiting the estrogen biosynthesis due to its competitive capability of the compound to act on the aromatasic system involved in the transformation of testosterone into estrogens.

More particularly, it has been found according to the present invention that the antiestrogen action of cyproterone acetate not only acts on the perimenopausal gynecological pathology caused by extrafollicular hyperestrogenism (such as cystic glandular hyperplasia of the endometrium) but also on other gynecological pathology wherein the hyperestrogenism responsible of this pathology is "intrafollicular".

According to the present invention, the following gynecological pathology has been treated such as for example:
(a) fibromatosis and myomatosis of the uterus,
(b) menometrorrhagia in normal uterus with persistence of proliferative phase of the endometrium and
(c) fibrocistic mastosis.

As illustrated by the following examples, the results so obtained have shown the antiestrogen action of cyproterone acetate on the ovaric cells entitled to the estrogen biosynthesis.

It has been also shown that the above pathology is supported by hyperestrogenism since only the use of an antiestrogen molecule, such as cyproterone acetate, acting directly on the estrogen biosynthesis allows to obtain:

reduction of fibromyomatosis of the uterus,
reduction up to the disappearance of myomas of the uterus,
reduction of fibromatosis and disappearance of mastodynias and normalization of menometrorrhagic cycle for the persistance of proliferative phase of the endometrium.

The important aim reached by the present invention is not that, as expected, of using cyproterone acetate as a progestinic agent to the cells already reached by the estrogen signal, but that of preventing this signal from reaching these cells with a molecule, such as cyproterone acetate, capable of eliminating the estrogen signal.

This peculiar antiestrogen action of cyproterone acetate, object of the present invention, shows that this compound, besides the above gynecological pathology, is especially useful in the antiestrogen prevention and therapy of the estrogendependant tumors in women, that is mammary and endometrium tumors.

The following examples illustrate the use of cyproterone acetate, its dosages and pharmacological effects according to the invention. In the following treatments, the compound has been administered by oral route, at the dose of from 25 to 200 mg/day.

The dosages used and the number of cycles of treatment depend on the kind of pathology and of the age of the patients to be treated.

More precisely, the following dosages have been used:
(1) cycles of 50 mg/day from the 13th to the 24th day of the menstrual period in women if the sexual cyclic biorhythm is to be maintained and in the absence of alarm pathology (mammary and endometrium adenocarcinoma, cystic glandular hyperplasia of the endometrium, risky fibromastosis).
(2) Cycles of 50+50 mg/day or 100+100 mg/day for a period of 20 days/month (according to the obesity and body surface) in women if the sexual biorhythm is not necessarily to be maintained (menopause and perimenopause) or in the presence of a risky pathology even in pre-menopause.

The therapy is interrupted when the expected results are reached, being said results valuated on the ground of the clinic and anamnestic objectiveness, hormonal dosages, echographias, mammographies, thermographies, histologic and cytologic tests.

EXAMPLE 1

8 women, aged from 39 to 45, affected with uterine fibromyomatosis were treated with cyproterone acetate.

In cases of voluminous fibromyomatosis it was noticed a normalization of menstrual flux, if menometrorrhagic, and stabilization of the volume of the uterus during the treatment.

In light entity fibromatosis (10–12 cm diameter), a reduction of about 2 cm of the uterine diameters was noticed. Also in small myomas (3-4 cm diameter), a reduction up to disappearance of myomatous nodus.

One case of total disappearance of a 3 cm myomatous nodus after 1 year therapy with cyproterone acetate, at the dose of 50 mg/day from the 14th to the 24th of the menstrual period, with pelvic echographic control before and after the treatment, had been previously treated for many months with medroxyprogesterone acetate (MPA) without any positive result.

EXAMPLE 2

8 women, aged from 38 to 46, with normal uterine volume and continuous proliferative phase of the endometrium, soffering from menometrorrhagies, were treated with cyproterone acetate.

After a 4-6 months cyclic therapy with 50 mg/day from the 14th to the 24th day, stabilization of the quantity of menstrual flux was obtained and the menometrorrhagia stopped since the first month of treatment.

EXAMPLE 3

6 women affected with fibrocystic mastosis were treated with 50 mg of cyproterone acetate from the 14th to the 24th day. During the treatment it was noticed the disappearance of the mastodynias and mammary tension and, in some cases a remarkable reduction of fibromastosis.

What is claimed is:

1. A method of treating functional and tumoral estrogen-dependent pathology caused by intrafollicular iperestrogenism, which comprises:
   administering to a subject a therapeutically effective amount of cyproterone acetate which blocks the estrogen signal in said subject.

2. A method of treating gynecologic pathology caused by iperestrogenism intrafollicular in women having active menstrual cycles, which comprises:
   administering to a subject a therapeutically effective amount of cyproterone acetate which inhibits estrogen biosynthesis of the cells of granulosa and the luteinic cells of ovarian folliculus.

3. A method of treating uterine fibromatosis and myomatosis, menometrorrhagia in normal uterus with persistence of the proliferative phase of the endometrium and fibrocystic mastosis, which comprises:
   administering to a subject a therapeutically effective amount of cyproterone acetate.

4. The method of claim 1, 2, or 3, wherein the dosage of cyproterone acetate administered ranges from 25 mg to 200 mg/day for a number of cycles of treatment which are determined by the pathology being treated and the age of the subject.

* * * * *